United States Patent
Wang et al.

(10) Patent No.: US 8,556,958 B2
(45) Date of Patent: Oct. 15, 2013

(54) RECOVERABLE VALVE STENT

(75) Inventors: Tao Wang, Beijing (CN); Kunling Tian, Beijing (CN)

(73) Assignee: Beiging Puyishengji Medical Technology Co., Ltd., Beijing (CN)

( * ) Notice: Subject to any disclaimer, the term of this patent is extended or adjusted under 35 U.S.C. 154(b) by 326 days.

(21) Appl. No.: 12/790,123

(22) Filed: May 28, 2010

(65) Prior Publication Data

US 2010/0234937 A1 Sep. 16, 2010

(30) Foreign Application Priority Data

Nov. 28, 2007 (CN) .......................... 2007 1 0195409

(51) Int. Cl.
*A61F 2/82* (2013.01)
*A61F 2/24* (2006.01)

(52) U.S. Cl.
USPC ........................................ 623/1.15; 623/1.18

(58) Field of Classification Search
USPC ............................................... 623/1.11–1.59
See application file for complete search history.

(56) References Cited

U.S. PATENT DOCUMENTS

| | | | |
|---|---|---|---|
| 6,357,104 B1 * | 3/2002 | Myers | 29/527.1 |
| 6,792,979 B2 * | 9/2004 | Konya et al. | 140/92.1 |
| 7,048,014 B2 * | 5/2006 | Hyodoh et al. | 140/92.1 |
| 2009/0099643 A1 * | 4/2009 | Hyodoh et al. | 623/1.15 |
| 2010/0069916 A1 * | 3/2010 | Cully et al. | 606/108 |
| 2010/0087913 A1 * | 4/2010 | Rabkin et al. | 623/1.16 |
| 2011/0166637 A1 * | 7/2011 | Irwin et al. | 623/1.13 |

* cited by examiner

*Primary Examiner* — Suzette J Gherbi
(74) *Attorney, Agent, or Firm* — Dunlap Codding, P.C.

(57) ABSTRACT

A recoverable, safe and reliable valve stent for unidirectional flow of human lumen which can be implanted temporarily or for a long term and is used in the interventional therapy so as to obstruct from anisotropic flow, in the case of lung diseases. It comprises a cylindrical stent made up of memory alloy material. In particular, an elastic diaphragm is arranged inside the cylindrical stent and at least one gap is arranged on the diaphragm so that the spring piece is divided into a bendable section. One end of the cylindrical stent is provided with a fixed rear clip which is used to fix the alloy material making up the cylindrical stent. The rear clip is provided with screwthreads which can be connected with the conveyor. The stent in the present invention is in a structure without hook body, so the stent can be accurately positioned, adjusted and placed or recovered in double directions with strong anti-backflow ability.

12 Claims, 7 Drawing Sheets

RECOVERABLE VALVE STENT

CROSS-REFERENCE TO RELATED APPLICATIONS

This application claims priority and benefit under 35 U.S.C. 120 and 365(c) as a continuation of International application No. PCT/CN2008/001941 which was assigned an international filing date of Nov. 28, 2008 and associated with publication WO 2009/079915 and which claims priority under 35 U.S.C. 365(b) to Chinese Application 200710195409.3 filed on Nov. 28, 2007, the disclosures of which are expressly incorporated herein.

FIELD OF THE INVENTION

The present invention relates to a medical instrument, more particularly, to a valve stent for unidirectional flow of human lumen which is used in the interventional treatment for treating diseases of lung and obstructing anisotropic flow.

BACKGROUND OF THE PRESENT DISCLOSURE

Emphysema, bullae and chronic obstructive pulmonary disease, etc. are the common diseases involving the lung. Besides treatment methods like infection resistance with drugs, the surgery is generally based on lung volume reduction surgery. As the patients generally have weak physique and poor pulmonary function, they cannot tolerate the surgery so that a high death rate is caused, and part of the patients cannot be effectively treated or radically cured. Along with maturity of interventional therapeutic methods and technologies, a technology is developed that a stent and a one-way valve are placed in the trachea or bronchial tube below the trachea in the target region of the patient's lung. The one-way valve is opened in case of expiration and is closed in case of inspiration so as to reduce the residual volume at the pathologic lung and discharge the secretions, finally cause the collapse or fibrosis of pathologic lung and exert the compensation of healthy lung's gradual expansion and improve the patient's lung function. Since gall bladder, bile duct and aortic valves of blood have pathological changes or the human lumen has anisotropic flow, so similarly the anisotropic flow needs to be resisted. The stent is provided with a hook body made of elastic metal. After the stent is placed into the lumen, the hook body is penetrated into the wall surface of lumen to position the stent. The hook body has the insuperable shortcomings. For example, since the hook body may cause a different degree of damage to the wall surface of human lumen, complications like puncturing and long-standing inflammation may be produced, and especially displacement of the stent due to larger stress may happened, and then the wall surface of lumen is scratched. Another shortcoming is that after the stent is positioned, if the stent is damaged and deviated or the one-way valve is damaged, the stent can be taken out from the human body only by an operation. Moreover, once the stent is placed into, it cannot be adjusted, so the prior interventional stent and one-way valve urgently need to be improved.

DISCLOSURE OF THE INVENTION

The object of the present invention is to provide a recoverable, safe and reliable valve stent which can be implanted temporarily or for a long term and is used in the interventional therapy for unidirectional flow of human lumen, so as to obstruct from anisotropic flow in the case of diseases of lung, bile duct and aortic valve.

A technical solution for realizing the present invention is as follows: a recoverable valve stent, comprising a cylindrical stent made up of memorial alloy material in which an elastic diaphragm is arranged, wherein there is at least one gap on the diaphragm so that the diaphragm forms a flexible spring piece, one end of the cylindrical stent is provided with a fixed rear clip which is used for fixing the cylindrical stent structured with the memorial alloy material and is equipped with screwthreads which can be connected to a conveyor.

A thread of the memorial alloy material is weaved into the cylindrical stent and forms at least one bundle of alloy wire which is fixed with the rear clip, so that the end of the cylindrical stent which fixed with the rear clip forms at least one opening.

A thread of the memorial alloy material is weaved into the cylindrical stent and forms at least one bundle of alloy wire bundle which is fixed with the rear clip located at the upper edge of the wall of the cylindrical stent, so that the end of the cylindrical stent which fixed with the rear clip forms at least one opening in roughly round shape.

A thread of the memorial alloy material is weaved into the cylindrical stent and forms at least two bundles of alloy wire which are fixed with the rear clip locating at the axis of the cylindrical stent, so that the end of the cylindrical stent which fixed with the rear clip forms at least two openings in sub-oval or roughly oval shape.

A thread of the memorial alloy material is weaved into the cylindrical stent and forms at least three or four bundles of alloy wire which are fixed with the rear clip locating at the axis of the cylindrical stent, so that the end of the cylindrical stent which fixed with the rear clip forms at least three or four openings.

The cylindrical stent is a netlike stent obtained through laser etching treatment to an alloy steel tube, and etched parts of it are in rhombus shape, one end of the stent is provided with at least three supports which are integral with the stent and are connected with the rear clip.

The cylindrical stent is formed by coiling at least one alloy wire, preferably by coiling two to four alloy wires, and one end of the cylindrical stent is provided with the rear clip.

The other end of the cylindrical stent is provided with a front clip, and the front clip and the rear clip are arranged symmetrically or asymmetrically.

The diaphragm is provided with a cylindrical section which is fit to the cylindrical stent, and one end of the cylindrical section is arranged integrally with a convex surface raising towards the center of a circle which has one unclosed round gap on it, so that the bendable spring piece is formed.

The diaphragm is provided with a cylindrical section which is fit to the cylindrical stent, and one end of the cylindrical section is arranged integrally with a convex surface raising towards the center of a circle which has two arch gaps symmetrically arranged and connected by a straight gap on it so as to form an I-shape gap, so that the spring piece is separated into two bendable sections.

The diaphragm is provided with a cylindrical section which is fit to the cylindrical stent, and one end of the cylindrical section is arranged integrally with a convex surface raising towards the center of a circle which has three branched gaps being arranged equiangularly and extending from the center of a circle towards periphery of it, the spring piece is separated into three bendable sections.

The diaphragm is provided with a cylindrical section which is fit to the cylindrical stent, and one end of the cylindrical section is arranged integrally with a convex surface raising towards the center of a circle which has cross-branched gaps extending from the center of a circle towards periphery of it, the spring piece is separated into four two bendable sections.

Each spring piece of the diaphragm is provided with a curved sunken part.

The thickness of the spring piece gradually diminishes from circumference to the convex center of the circle, and there is a cylinder at the intersecting position of the cylindrical section and the convex surface.

There are metal wire supports which can increase elastic deformation and strength of the spring piece, and are arranged inside of the spring piece or on its surface.

The spring piece is a thin slice with raised center of a circle which has a diameter matching that of the cylindrical stent, the spring piece is connected with one clip of the cylindrical stent by means of a metal rod, and at least two gaps, preferably three to four gaps, which extend from the position near the center of the circle to the edge of the spring piece are arranged so as to separate the spring piece into at least two sections.

The stent in the present invention has a structure without hook body, so as to avoid the damage of the hook body to the wall surface of human lumen and the occurrence of complications, and the stent can be accurately positioned and adjusted. When the stent is being placed or recovered, the doctor can at least have one viewable point. The stent also can be placed or recovered in a double direction, so it is safe and reliable. The structure of the one-way valve is reasonable and it has the characteristics of the human heart valve, like strong anti-backflow ability, reliability and durability. It is a unidirectional valve stent which is used in the interventional therapy for unidirectional flow of human lumen, so as to obstruct from anisotropic flow, such as in the case of diseases of lung, bile duct and aortic valve.

DETAILED DESCRIPTION

Figure 1:
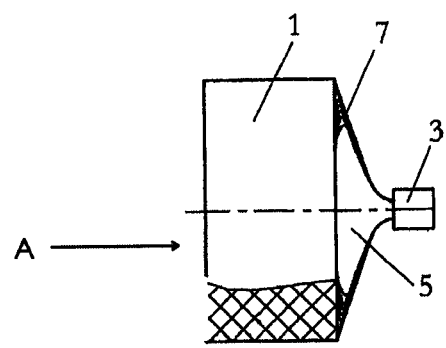
FIG. 1 is a structure diagram of a first embodiment of a stent.
Figure 2:
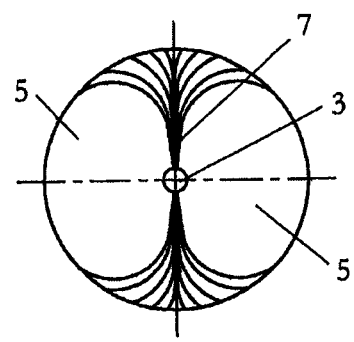
FIG. 2 is a right view of the stent in FIG. 1.
Figure 14:
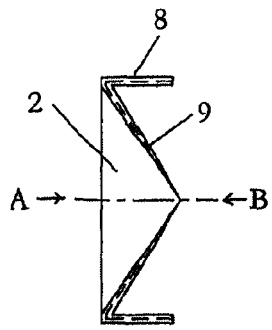
FIG. 14 is a sectional view of a first embodiment 1 of a diaphragm.
Figure 15:
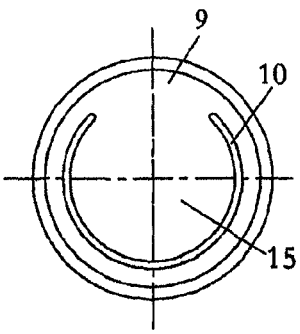
FIG. 15 is a structure diagram of a first embodiment of a spring piece.
Figure 53:
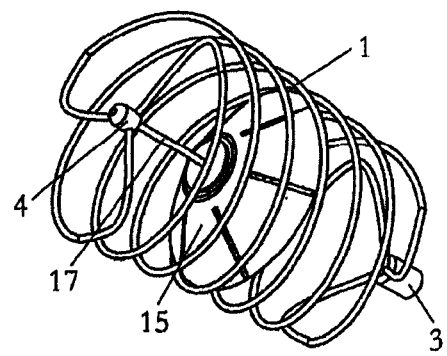
FIG. 53 is a solid state diagram of the invention in FIG. 51.

FIGS. 1-53 show embodiments of the present invention. Referring to FIGS. 1-2, a recoverable valve stent comprises a cylindrical stent 1 made up of memory alloy material in which an elastic diaphragm 2 (FIG. 14) is arranged. At least one gap 2a is arranged on the diaphragm 2 so that diaphragm 2 forms a bendable spring piece 15 (FIG. 15). One end of the cylindrical stent 1 is provided with a fixed rear clip 3 which is used to fix the alloy material which forms the cylindrical stent 1 and the rear clip 3 is provided with screwthreads which can be connected with the conveyor. The memory alloy materials are nickel-titanium alloy wires or alloy steel tubes. The cylindrical stent 1 is a cylindrical hollow tube which can be made by weaving multiple alloy wires or by spirally coiling one or multiple alloy wires. It can also be etched with alloy steel tubes. The elastic diaphragm 2 is arranged in the cavity of the cylindrical stent 1, and the diaphragm 2 is made of polyester, polytetrafluoroethylene, polyurethane, medical silica gel or polyester fabrics. at least one gap arranged on the diaphragm 2 so that the diaphragm 2 forms the bendable spring piece 15. One end of the cylindrical stent 1 is provided with the fixed rear clip 3 which is used to fix the alloy material that forms the cylindrical stent. The rear clip 3 is a cylinder, the external end face of which is provided with an internal thread or on which a tapping thread is arranged. The cylindrical stent 1 is provided with a preset expandable shape with relative elongation. It is spirally connected with the guide wire of a tubular conveyor via the screwthreads of the rear clip 3. The cylindrical stent 1 draws back into the conveyor at a retraction state and it stretches out from the end part of the conveyor when being released. When the cylindrical stent 1 is completely released from the conveyor, its preset shape laterally extends and is tightly combined and positioned with the inner wall of the human lumen, and then the elastic spring piece 15 formed by the gap on the diaphragm 2 produces the unidirectional bending under the action of gas or liquid, to open or close the opening formed in the diaphragm 2 and to enable the unidirectional flow or obstruct flow of gas or liquid. The cylindrical stent 1 is mounted into the conveyor in a compression and stretching way through the spiral connection of the rear clip 3 and the guide wire in the conveyor and then is placed into the human lumen via the conveyor, or the cylindrical stent 1, which has been placed into the human lumen, is recovered through the spiral connection of the guide wire in the conveyor and the rear clip 3. The rear clip 3 makes the cylindrical stent 1 have one viewable point.

Figure 6:
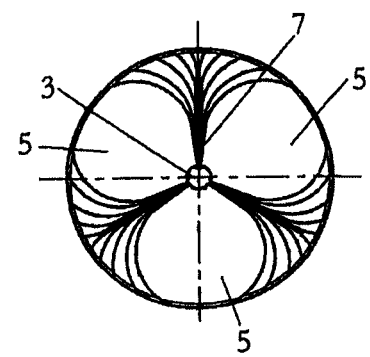
FIG. 6 is a right view of the stent in FIG. 5.
Figure 7:
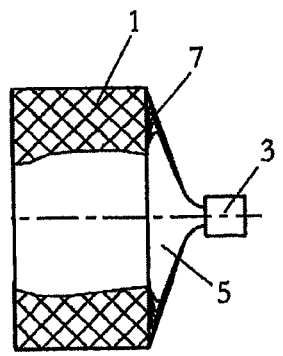
FIG. 7 is a structure diagram of a fourth embodiment of a stent.
Figure 8:
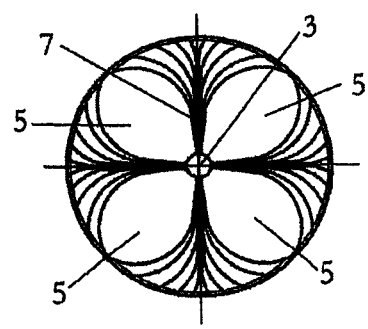
FIG. 8 is a right view of the stent in FIG. 7.

At least one alloy wire bundle 7 is formed and then fixed with the rear clip 3 after the threadlike memory alloy material in wire structure are weaved into the cylindrical stent 1. Then the end of the cylindrical stent 1 provided with the rear clip 3 forms at least one opening 5. The cylindrical stent 1 is a cylindrical hollow net-like tube which is weaved with a mould by multiple nickel-titanium alloy wires. One end of the tube is in opened shape and the net surface of which is in grille shape. After the hollow net-like tube is formed, the alloy wires at the other end of the tube will not be weaved in a net shape from this end, but form at least one alloy wire bundle 7 after being gotten together in a single wire shape. The alloy wire bundle 7 is fixed with the rear clip 3, and at least one opening 5 is formed at one end of the cylindrical stent 1 arranged with the rear clip 3. The opening 5 can permit the gas or liquid to flow through. Referring to FIGS. 1-2, two alloy wire bundles 7 are formed and then fixed with the rear clip 3 located at the axle position of the cylindrical stent 1 after the threadlike memory alloy material are weaved into the cylindrical stent. Then the end of the cylindrical stent 1 provided with the rear clip 3 forms two roughly elliptic openings 5. After the hollow net-like tube is formed, the alloy wires at the other end of the tube will not be weaved in a net shape from this end, but are equally divided into two alloy wire bundles 7, and the alloy wires of each alloy wire bundle 7 are bent towards the center of circle of the tube in a single wire shape, and then transitionally curved and gathered together. The two alloy wire bundles 7 slant oppositely to the center of circle of the tube at the same time, and its tail wires are fixed by the rear clip 3 located at the axle of the tube, to form a rough taper (see FIG. 1) and form two opposite roughly elliptic openings 5, see FIG. 2. The gas or liquid entering from the opening A on the end face of the cylindrical stent 1 is shunted by two openings 5 and then flow through these two openings. As the two alloy wire bundles 7 forms an integrated structure with the cylindrical stent 1 via the rear clip 3, a support is formed to enhance the radial supporting force of the cylindrical stent. The rear clip 3 makes the cylindrical stent 1 to have a viewable point at the axle of the cylindrical stent 1. Three or four alloy wire bundles 7 are formed by alloy wires which are weaved into the cylindrical stent 1, and then are fixed by the rear clip 3 at the axle of the cylindrical stent 1. Three or four openings 5 (see FIGS. 5-8) are formed at one end of the cylindrical stent 1 arranged with rear clip 3. Multiple alloy wires are equally divided into three alloy wire bundles 7, the tail wires of the three alloy wire bundles 7 are fixed by the rear clip 3 and then equally divided into three roughly round openings 5 (see FIG. 6) on the tapered surface. These three openings 5 can reduce the small flow section as well as the flow volume, and forms four supports to enhance the radial supporting force of the stent 1. The said alloy wires also can be divided into multiple alloy wire bundles 7 so as to form multiple openings 5. But the number of openings 5 is selected depending on the required gas or liquid flow. The data obtained in the experiments indicate that the number of openings 5 are preferably 1 to 4. If the number of openings 5 exceed 4, the ability of gas or liquid flow passing through will reduce as the quantity of gas or liquid flow increases. The excess reduction in the flow volume of gas or liquid doesn't have practical significance.

Figure 3:
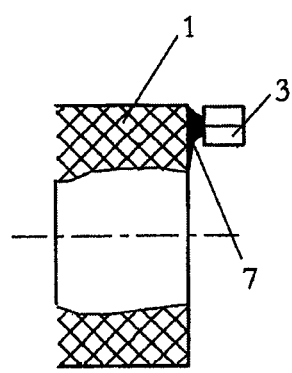
FIG. 3 is a structure diagram of a second embodiment of a stent.
Figure 4:
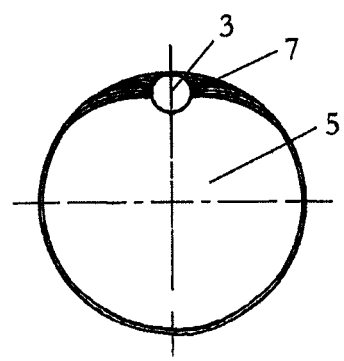
FIG. 4 is a right view of the stent in FIG. 3.
Figure 5:
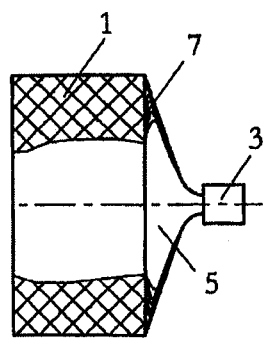
FIG. 5 is a structure diagram of a third embodiment of a stent.

Referring to FIGS. 3-4, one alloy wire bundle 7 is formed and then fixed at the rear clip 3 located at the upper edge of the lateral wall of the cylindrical stent 1 after the said threadlike memory alloy material are weaved into the cylindrical stent. Then the end of the cylindrical stent 1 provided with the rear clip 3 forms one roughly round opening 5. In order to make the threadlike cylindrical stent 1 have the maximum drift diameter, after the threadlike cylindrical stent 1 is weaved into a cylinder through multiple alloy wires, the alloy wires at one end of the cylindrical stent 1 get together on one lateral wall towards this end, converge into an alloy wire bundle 7 and then be fixed with the rear clip 3 located at the upper edge of the lateral wall (see FIG. 3), so that a roughly round opening 5 (see FIG. 4) with diameter approximating the diameter of the cylindrical stent 1 is formed. This opening permits the gas or liquid to flow through at a maximum flow rate, so the cylindrical stent 1 has maximum flow diameter to exert minimal impact on the flow rate.

Referring to FIGS. 38-41, a front clip 4 is also arranged at one end of the said cylindrical stent 1, and the front clip 4 and the rear clip 3 can be arranged symmetrically or asymmetrically; in order to realize the bidirectional placement or recovery of the cylindrical stent 1, after it is weaved into a tube, the alloy wires at its one end are divided into alloy wire bundles 7 and then fixed with the front clip 4, and opposite openings 5 formed at both ends of the cylindrical stent 1; if three alloy wire bundles are provided, three opposite openings (see FIG. 41) will respectively form at both ends of the threadlike cylindrical stent 1 and the front clip 4 and the rear clip 3 are at a symmetrical state (see FIG. 40) at the axle line of the cylindrical stent 1. The front clip 4 and the rear clip 3 arranged symmetrically are suitable for the threadlike stent 1 with more than one alloy wire bundles, while the other end of the net-like stent 1 obtained through laser etching is also provided with supports 6 which are fixed with the front clip 4, so both ends of the stent obtained through laser etching are respectively provided with a clip; for the cylindrical stent 1 with the maximum drift diameter, the front clip 4 and the rear clip 3 are arranged asymmetrically, that is, the front clip and the rear clip are respectively arranged on the opposite lateral walls at both ends of the cylindrical stent 1 and are parallel to the axle line of the cylindrical stent 1 (see FIG. 38). A roughly round opening 5 with diameter approximating the diameter of the cylindrical stent 1 (See FIG. 39) respectively forms at both ends of the cylindrical stent 1, and an internal thread is also arranged on the external end face of the front clip 4, or a tapping thread is arranged on the cylinder, so the front clip 4 is connected with or separated from the conveyor through the thread. By use of the front clip 4 and the rear clip 3, both ends of the said cylindrical stent 1 are respectively provided with a clip and thus the cylindrical stent 1 has two viewable points and the doctor can release or recover the cylindrical stent 1 through the front clip 4 or the rear clip 3. The said viewable point refers to the point which is easy to be reflected under ultrasonic wave or X ray. Under the directions of viewable points, the doctor can easily conduct placement and positioning, and also can place or recover the cylindrical stent 1 by choosing the front clip 4 or the rear clip 3 in different directions according to the actual situation, so as to realize the unidirectional placement or recovery and make the operation more convenient and safer.

Figure 34:
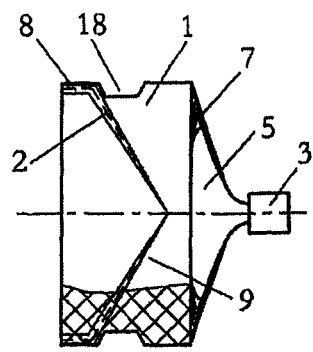
FIG. 34 is an integral structure diagram of the first embodiment of the present invention

In order to enhance the radial strength of the threadlike cylindrical stent 1, at least one sunken ring 18 is arranged on the said threadlike cylindrical stent 1, the section of the sunken ring 18 is a trapezoid (see FIG. 34). The sunken ring 18 not only can enhance the radial supporting strength of the threadlike cylindrical stent 1, but also make the inner wall of the human lumen extrude into the stent to form an inlay between the stent and the inner wall of the human lumen and maintain the steady positioning of the threadlike cylindrical stent 1. A bevel edge 21 of the sunken ring 18 forms a supporting and sealing effect on the diaphragm 2 placed in the threadlike cylindrical stent 1.

Figure 9:
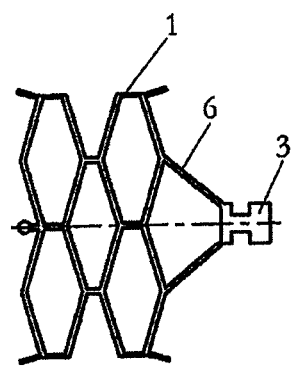
FIG. 9 is a structure diagram of a fifth embodiment of a stent.
Figure 10:
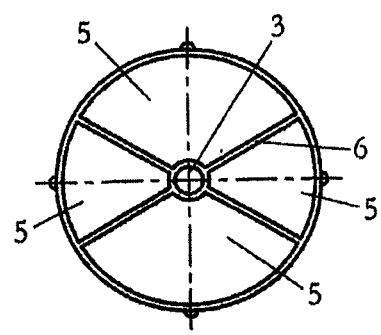
FIG. 10 is a right view of the stent in FIG. 9.

Referring to FIGS. 9-10, the said cylindrical stent 1 is a net-like stent obtained through laser etching of alloy steel tube, the shape of the etched part approximates a rhombus, one end of the stent is provided with at least three supports 6 integrated with the stent, and the supports 6 are connected with the rear clip 3; the cylindrical stent 1 is formed through the laser etching of one alloy steel tube, and the shape of the etched part of the alloy steel tube approximates a rhombus. A rhombic grille-shaped cylinder (See FIG. 9) is formed, and it has a large radial supporting ability and has a better inlayed support with the inner wall of the human lumen. In order to facilitate the placement or recovery of the cylinder, one end of the cylindrical stent 1 is provided with linear supports 6 obliquely extending towards the axle line of cylindrical stent 1, supports 6 are integrated with the cylindrical stent 1 and one end of the supports 6 is connected with the rear clip 3 (See FIG. 10). At least three supports 6 are provided, and four supports are preferred. The other end of the cylindrical stent 1 also can be provided with supports 6, so both ends of the cylindrical stent 1 are respectively provided with a clip and then the cylindrical stent 1 can be placed or recovered in a double direction.

Figure 11:
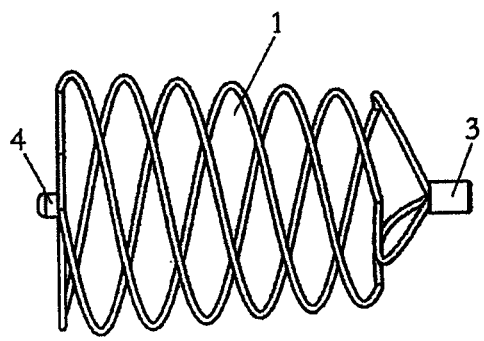
FIG. 11 is a structure diagram of a sixth embodiment of a stent.
Figure 12:
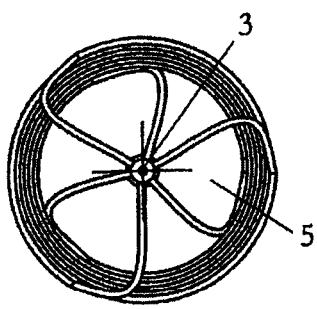
FIG. 12 is a right view of the stent in FIG. 11.
Figure 13:
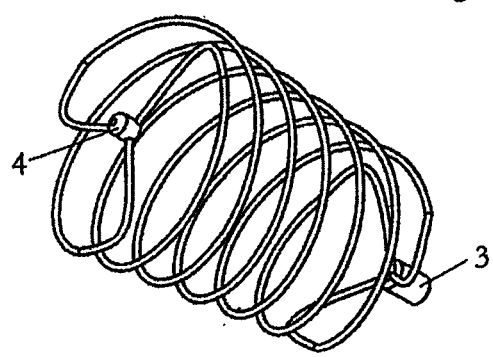
FIG. 13 is a perspective drawing of the stent in FIG. 11.

Referring to FIGS. 11-13, the said cylindrical stent 1 is spirally formed by at least one alloy wire, its one end is provided with the rear clip 3, and two to four alloy wires are preferably chosen; the cylindrical stent 1 forms a spiral cylinder after being spirally wound by one or a plurality of alloy wires, and the number of alloy wires is preferably 2 to 4. By taking three alloy wires as an example in this embodiment (see FIG. 13), one end of the three alloy wires is respectively fixed with the rear clip 3, and then is spirally wound along the axial direction of the rear clip 3 with uniform distribution of equal angles while the rear clip 3 is used as the center of a circle. Each spiral coil is wound into a spiral cylinder in a form of diameter increase, and then the other end of the alloy wires is firmly welded together or is fixed by a front clip 4. The diameter of the formed spiral cylinder close to the front clip 4 is slightly larger than that of the spiral cylinder close to the rear clip 4 (see FIG. 11), so a frustum shape is formed. The frustum-shaped spiral body has good inlaying capability with the inner wall of the human lumen, and three alloy wires of the cylindrical stent 1 fixed by the rear clip 3 form three openings 5 on this end face, and these three openings are staggered with the three openings formed by the alloy wires fixed by the front clip 4 (see FIG. 12). The spiral cylindrical stent 1 can greatly reduce the usage amount of alloy wires and has a higher supporting force. As the spiral stent can be made into the stent with a very small diameter and a great contractive pressure and stretching deformation, the stent can be mounted into the conveyor with an extremely small diameter and then be placed into the human lumen with a very small diameter, and the spiral stent with a large diameter can be released or recovered through the conveyor with a small diameter, to avoid the possible damage to the inner wall of the lumen by use of the conveyor with a large diameter. The spiral stent contacts with the wall surface of the human lumen, so the wall surface will have certain roughness to increase the stability.

Figure 16:
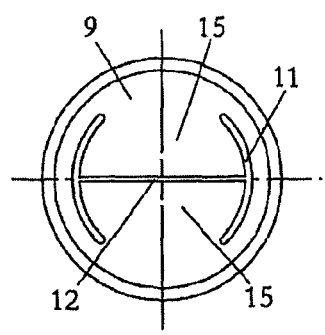
FIG. 16 is a structure diagram of a second embodiment of a spring piece.
Figure 17:
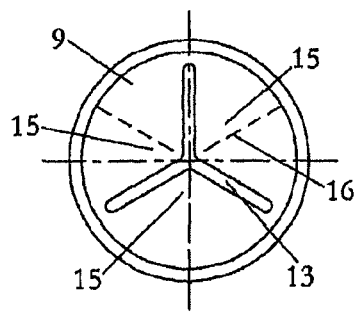
FIG. 17 is a structure diagram of a third embodiment of a spring piece.
Figure 18:
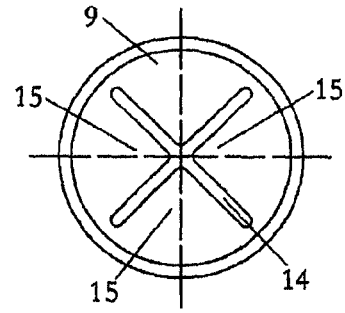
FIG. 18 is a structure diagram of a fourth embodiment of a spring piece.

The said diaphragm 2 is provided with a cylindrical section 8 adaptive to the cylindrical stent 1. One end of the cylindrical section 8 is integrally connected with a convex surface 9 uplifted towards the center of the circle, and an unclosed round gap 10 is arranged on the convex surface 9; or two symmetrical cambered gaps 11 are arranged and a linear gap 12 arranged between the two cambered gaps 11 make the two symmetrical cambered gaps connected to form a nearly H-shaped gap; or a triangular gap 13, which takes the center of circle as starting point and makes the equal included angle extend toward the circumference, is arranged; or a cross-shaped gap 14, which takes the center of circle as starting point and makes the equal included angle extend toward the circumference, is arranged; and then one to four bendable spring pieces 15 are respectively formed. By referring to FIG. 14, the diaphragm 2 is a cylinder, the outer diameter of its cylindrical section 8 is adaptive to the inner diameter of the cylindrical stent 1 and the cylindrical section 8 is also arranged in one end of the cylindrical stent 1. The cylindrical section 8 with one end open is integrated with the cylindrical stent 1, in which a cone uplifted towards the center of the circle is arranged. The bottom side of the cone is integrally connected with that of the cylindrical section 8, while the cone side forms the convex surface 9. The thickness of the convex surface 9 gradually decreases from the bottom side of the cone to the uplifted position of the center of circle. The section of the diaphragm 2 looks like a vertical M shape (see FIG. 14). A very fine gap cut by the cutter is arranged on the convex surface 9, and this gap presents an unclosed round gap 10 which makes the convex surface 9 form a nearly 75% round flaky spring piece 15 (see FIG. 15), and the section of the spring piece 15 presents a V shape. When the diaphragm 2 is not forced by an external force, the spring piece 15 is laminated with the convex surface 9 to form a closed surface. When the gas or liquid enters from the bottom A of the diaphragm 2, the gas or liquid gathers towards the top of the cone and then moves towards the gap gate along the inner wall surface of the tapered convex surface 9, so the spring piece 15 bends upward to open an angle by taking the linking section between the spring piece 15 and the diaphragm 2 as a pivot point, and the convex surface 9 at a closed state forms an opening, and thus the gas or liquid can flow out from this opening, and the opening of the spring piece 15 can be increased as the gas or liquid flow rate increases; if the gas or liquid enters from the top B of the diaphragm 2 in a reverse direction, the gas or liquid is divided into two vortexes by the tapered convex surface 9, so most of the pressure is transferred to the inner wall surface of the cylindrical section 8. Meanwhile, the spring piece 15 is extruded, so it can be tightly clamped with the round gap 10 to form a closed surface and thus obstruct the flow of gas or liquid; the diaphragm 2 forms a one-way valve, with one-way clearance function and certain anti-backflow ability. When the pressure is very high, a little gas or liquid leaks from the fitting clearance between the spring piece 15 and the round gap 10, but will not exert an influence. Additionally, the length (axial length) of the cylindrical section 8 can be increased, so as to increase the bonding area between the cylindrical section and the stent; the said gap on the convex surface 9 can be a nearly H-shaped gap, which comprises two symmetrical cambered gaps 11 and one linear gap 12; the linear gap 12 is located between the two cambered gaps 11, and also makes the two cambered gaps 11 communicated with each other. The H-shaped gap makes the convex surface 9 forming two opposite nearly semicircular spring pieces 15 (see FIG. 16); these two spring pieces can bend upward or downward, to open an opening; and the anti-backflow ability of the H-shaped gap is stronger than that of the round gap 9. Or the gap on the convex surface 9 is a triangular gap 13 which makes the convex surface 9 form three vertically opposite triangular spring pieces 15 (see FIG. 17) by taking the center of circle as starting point and making the equal included angle extend toward the circumference; the anti-backflow ability of these three spring pieces 15 is stronger than that of the H-shaped gap. Or the said gap on the convex surface 9 is a cross-shaped gap 14 which makes the convex surface 9 form four vertically opposite triangular spring pieces 15 (see FIG. 18); the anti-backflow ability of these four spring pieces 15 is stronger than that of the triangular gap. The said gap can also be a gap shaped like the Chinese character "Mi", to form a plurality of spring pieces, but the effect may decrease because of excess spring pieces.

Figure 19:
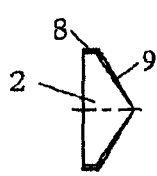
FIG. 19 is a sectional view of a second embodiment of a diaphragm.

The said diaphragm 2 is composed of a cylindrical section 8 and a cone (see FIG. 19). The diameter of the cone side of the cone is equal to that of the cylindrical section 8, while the bottom side of the convex surface 9 of the cone's cone side is integrated with the terminal side of the cylindrical section 8. The process for making the diaphragm 2 in this structure is quite simple.

Figure 20:
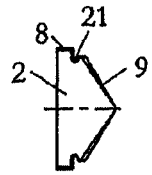
FIG. 20 is a sectional view of a third embodiment of a diaphragm.

The said diaphragm 2 is composed of a cylindrical section 8, a cylinder 21 and a cone (see FIG. 20). The diameter of the cylinder 21 is smaller than that of the cylindrical section 8 and the bottom diameter of the cone is smaller than that diameter of the cylindrical section 8 and larger than the diameter of the cylinder 21. The bottom side of the convex surface 9 formed by the cone side of the cone is integrated with one end side of the cylinder 21, while the other end of the cylinder 21 is connected with one end side of the cylindrical section 8. A groove is formed between the cylindrical section 8 and the cone via the cylinder 21, and the groove enables the diaphragm 2 to have certain deformation margin. Due to existence of this groove, after the cylindrical stent 1 is placed into the human body, the stent may be deformed to a certain degree because of compression, and then the cylindrical section 8 may be deformed accordingly. As the diameter of the cylinder 21 is smaller than that of the cylindrical section 8, the cylinder 21 only has a minor deformation with the deformation of the cylindrical section 8, so as to slow down the deformation, make the cone basically not affected by deformation, still maintain the original shape, prevent the cone from being not closed completely with the subsequent deformation of the cone, and then increase the elasticity of the whole diaphragm.

Figure 21:
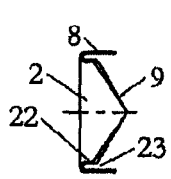
FIG. 21 is a sectional view of a fourth embodiment of a diaphragm.

The said diaphragm 2 is composed of a cylindrical section 8, a cylinder 22 and a cone (see FIG. 21). The diameter of the cylinder 22 is smaller than that of the cylindrical section 8 and is equal to the bottom diameter of the cone. The cylinder 22 and the cone are simultaneously placed in the cavity of the cylindrical section 8. The bottom side of the convex surface 9 of the cone is integrated with one end side of the cylinder 22, while the other end of the cylinder 22 is connected with the bottom side of the cylindrical section 8. A space 23 is formed between the outer wall of the cylinder 22 and the inner wall surface of the cylindrical section 8, and the space 23 has the same deformation margin function as the said groove. As the axial length of the cylindrical section 8 is longer, the contact surface between the cylindrical section and the stent increases and then the cylindrical section fits well with the stent.

Figure 22:
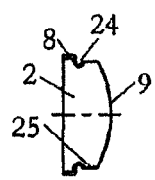
FIG. 22 is a sectional view of a fifth embodiment of a diaphragm.

The said diaphragm 2 is composed of a cylindrical section 8, a cylinder 24, a cylinder 25 and a spherical crown (see FIG. 22). The diameter of the cylinder 24 is smaller than that of the cylindrical section 8, while the diameter of the cylinder 25 is smaller than that of the cylindrical section 8 and is larger than that of the cylinder 24 and the bottom diameter of the spherical crown 26 is equal to the diameter of the cylinder 25. The cylindrical section 8, cylinder 24, cylinder 25 and spherical crown 26 are connected as one integral in sequence, and a groove is formed between the cylindrical section 8 and the cylinder 25 via the cylinder 24 and this groove has the same effect as the said groove; the convex surface 9 of the spherical crown 26 presents a spherical surface. Similarly, a very fine gap cut by the cutter is also arranged on this spherical surface. Such gap can be the unclosed round gap, the H-shaped gap, the triangular gap or the cross-shaped gap, to form the spring piece 15. The spherical crown 26 can avoid the gas or liquid being compressed, but open an angle of the spring piece 15, and the spherical crown 26 also has the good anti-backflow ability.

Figure 23:
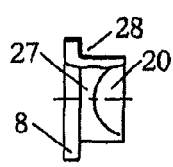
FIG. 23 is a sectional view of a sixth embodiment of a diaphragm.
Figure 24:
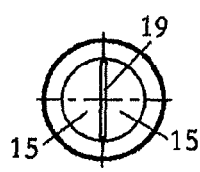
FIG. 24 is a right view of the diaphragm in FIG. 23.
Figure 25:
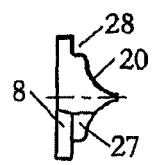
FIG. 25 is a vertical sectional view of the diaphragm in FIG. 23.
Figure 26:
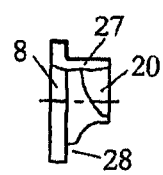
FIG. 26 is a sectional view of a seventh embodiment 7 of a diaphragm.
Figure 27:
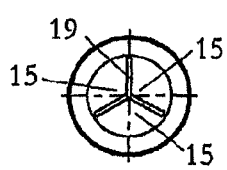
FIG. 27 is the right view of the diaphragm in FIG. 26.
Figure 28:
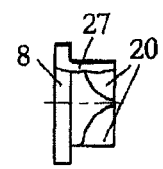
FIG. 28 is a sectional view of a eighth embodiment 8 of a diaphragm.
Figure 29:
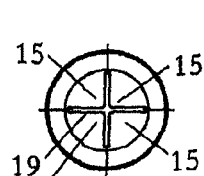
FIG. 29 is a right view of the diaphragm in FIG. 28.

Each spring piece 15 of the said diaphragm 2 is provided with a curved sunken part 20; the thickness of the said spring piece gradually diminishes from circumference to raised center of circle, and a cylinder is arranged at the interaction between the cylindrical section and the projecting piece. By referring to FIGS. 23-25, the diaphragm 2 is integrally connected by a cylindrical section 8 and a cylinder 27 (see FIG. 23), and a curved sunken part 20 is formed in the middle position near the cylinder 27. The two curved sunken parts 20 are opposite and their edges are joined together (see FIG. 25), and a straight fine gap (see FIG. 24) is formed at the joint between the two edges. The curved sunken part 20 on the cylinder 27 forms the spring piece 15. When the gas or liquid enters into the cylinder 27, the gas or liquid is compressed and then intensively impact the fine gap 19 on the top, so as to burst through the flaky spring piece 15 of the curved sunken part 20. The maximum opening of the spring piece 15 can reach the diameter of the cylinder 27, and also can be automatically adjusted as the flow rate changes. The flaky spring piece 15 with a curved sunken part 20 not only is favorable for the outflow of the forward gas flow, but also obstructs the flow of the reversed gas and increases the function of the diaphragm on the one-way valve; if the gas or liquid flows back, the pressure directly acts on the curved sunken part 20, to force the edges of the two spring pieces clamped with each other, seal the fine gap 19 and effectively prevent the backflow phenomenon; the spring piece with the curved sunken part 20 approaches the structure of human heat valve, so the spring piece has the best one-way sealing effect and the strongest anti-backflow ability. When the cylindrical section 8 is deformed under the radial pressure, the space 28 formed at the joint between the cylinder 27 and the cylindrical section 8 can make the cylinder 22 not be influenced by the deformation of the cylindrical section 8, but still be kept at its original state; the said cylinder 27 can be provided with three curved sunken parts 20, that is, the top of the cylinder 27 is kneaded together at a trisection angle, to form three vertically opposite curved sunken parts 20 (see FIG. 27) which form three spring pieces 15 and three vertically opposite straight fine gaps 19, with one-way sealing effect and anti-backflow ability further improved; or the top of the said cylinder 27 is kneaded together at a quartering angle, to form four vertically opposite curved sunken parts 20 which form four spring pieces 15 and four vertically opposite straight fine gaps 19 (see FIG. 29); a plurality of the said curved sunken parts can also be arranged, but it makes little sense to use more than four spring pieces. The best range is two to three spring pieces.

Figure 30:
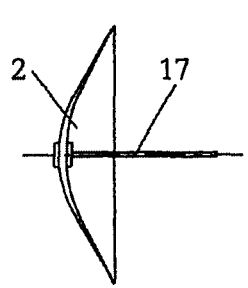
FIG. 30 is a sectional view of a ninth embodiment of a diaphragm.
Figure 31:
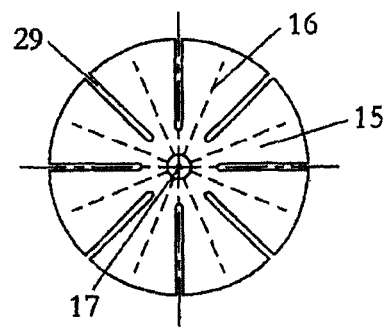
FIG. 31 is a right view of the diaphragm in FIG. 30.
Figure 32:
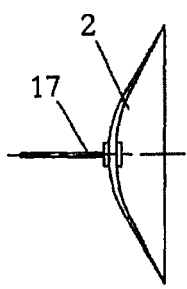
FIG. 32 is a sectional view of the tenth embodiment of a diaphragm.
Figure 33:
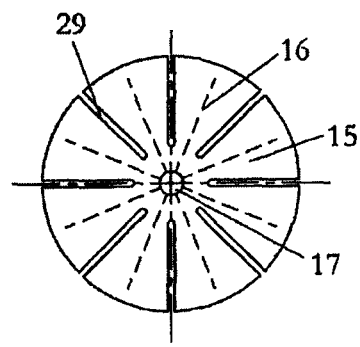
FIG. 33 is a right view of the diaphragm in FIG. 32.

The said spring piece 15 is a flaky object with the diameter adaptive to the diameter of the cylindrical stent 1 and a raised center of circle. The spring piece 15 is connected with one clip of the cylindrical stent 1 via a metal rod 17 (FIG. 3c), and at least two gaps 29 (FIG. 31) which extend from the position near the center of circle to the edge of the spring piece 15, to form at least two spring pieces 15, and three to four gaps 29 are preferably used; diaphragm 2 is an umbrella body (or called a bowl shape). The thickness of diaphragm 2 gradually diminishes from the top to the edge of the umbrella body (see FIG. 30), and the umbrella body is provided with a plurality of gaps 29, the length of which is smaller than the radius of the umbrella body, from the edge to the center of circle of the umbrella body. The gaps 29 are uniformly distributed at an equal angle while the center of the umbrella body is used as the center of a circle. The surface of the umbrella body connected between the two gaps 29 forms spring pieces 15. In order to make the spring piece 15 have certain strength, improve the elastic deformation of spring piece and enable it to have the shape memory characteristic, a metal wire support 16 is arranged inside or on the surface of the spring piece 15 (see FIG. 31). The metal wire support 16 is a memory alloy wire which can be covered in the spring piece or arranged on the surface of the spring piece. The support is equivalent to the ribs of the umbrella surface, which can play the role in forming and fixing to make each spring piece kept at a curved shape, and also can support the spring piece as a framework; in order to maintain the diaphragm 2 at an umbrella state, the top center of the umbrella body is firmly connected with a metal rod 17 which extends outward from the internal part of the umbrella body and then is firmly connected with the rear clip 3 of the cylindrical stent 1, looking like an opened umbrella. The metal rod 17 can make the spring piece formed by the gaps 29 make opening and closing movements around the metal rod, and maintain the fixed location of the diaphragm 2; the said metal rod 17 also can extend outward from the top surface of the umbrella body and then is firmly connected with the front clip 4 of the cylindrical stent 4 (see FIG. 32), the function of which is the same as the said metal rod. A plurality of gaps 29 can form a plurality of spring pieces 15, but three to four spring pieces 15 formed by three to four gaps 29 are preferred.

Figure 35:
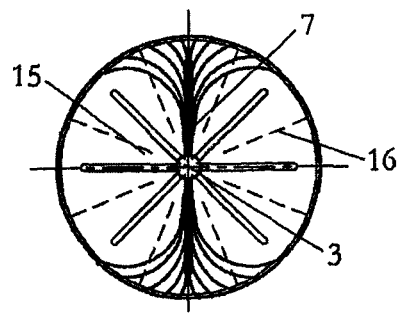
FIG. 35 is a right view of the invention in FIG. 34.

By referring to FIGS. 34-35, one end of the cylindrical stent 1 is open, while the other end forms two openings 5 after two alloy wire bundles 7 are fixed by the rear clip 3. The diaphragm 2 is placed in the cylindrical stent 1, and is integrated with the stent by seaming, laminating or direct forming on the stent. The bottom side of the cylindrical section 8 of the diaphragm 2 is level with the open edge of the cylindrical stent 1, and is jointly connected with the inner wall of the cylindrical stent 1. The bottom side of the tapered convex surface 9 of the diaphragm 2 tightly holds out against an embolic wall surface formed by a sunken ring 18 (see FIG. 34). The embolic wall surface of the sunken ring 18 forms one positioning point to the cylindrical section 8 and forms one supporting points to the convex surface 9, while this supporting point can enhance the anti-backflow ability and sealing effect of the diaphragm 2 in case of backflow; each spring piece (see FIG. 35) on the convex surface of the diaphragm 2 is provided with a support 16 (see FIG. 35) which is a memory alloy wire. As a framework, the support supports the spring piece and keeps the shape of the convex surface 9, so as to enhance the strength of the spring piece and make it have the shape recovery memory characteristic. In use, the guide wire in the conveyor lumen is spirally connected with the rear clip 3 of the cylindrical stent 1, so as to release or recover the cylindrical stent 1 in a single direction.

Figure 36:
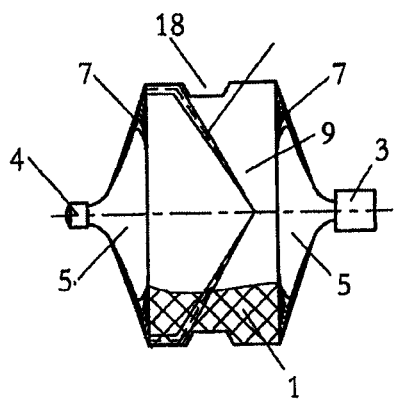
FIG. 36 is an integral structure diagram of the second embodiment of the present invention.
Figure 37:
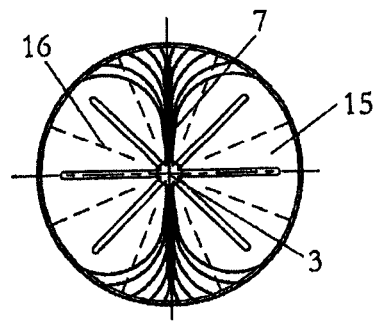
FIG. 37 is a right view of the invention in FIG. 36.

Referring to FIGS. 36-37, one end of the said cylindrical stent 1 forms two openings 5 after two alloy wire bundles 7 are fixed by the front clip 4, while the other end also forms two openings 5 after two alloy wire bundles 7 are fixed by the rear clip 3. The diaphragm 2 is placed in the cylindrical stent 1, and the bottom side of the diaphragm 2 holds out against the edge of the alloy wire bundles 7 fixed by the front clip 4 (see FIG. 36). Each spring piece on the convex surface 9 of the diaphragm 2 is provided with a support 16 (see FIG. 37). The guide wire in the conveyor lumen is spirally connected with the rear clip 3 or the front clip 4, so as to release or recover the cylindrical stent in a double direction. The said support which is a metal wire can be placed on the surface of the diaphragm, and also can be placed inside the diaphragm. If the diaphragm 2 is integrally processed or is composed of double-layer material, the support 16 can be placed between the two layers of material.

Figure 38:
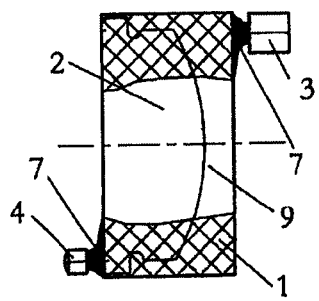
FIG. 38 is an integral structure diagram of the third embodiment of the present invention.
Figure 39:
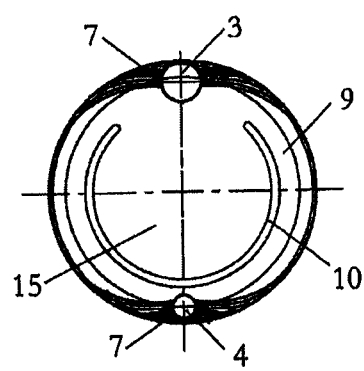
FIG. 39 is a right view of the invention FIG. 38.

Referring to FIGS. 38-39, the cylindrical stent 1 in a structure of a front clip 4 and a rear clip 3 is asymmetrically arranged. The convex surface 9 of the diaphragm 2 is a spherical surface, and the gap on the convex surface is an unclosed round gap (see FIG. 39). The unclosed round gap is matched with the cylindrical stent 1 which the front clip 4 and the rear clip 3 are arranged asymmetrically, so as to increase the flow area and also the flow rate, and thus release or recover the cylindrical stent 1 in a double direction through the front clip 4 or the rear clip 3.

Figure 40:
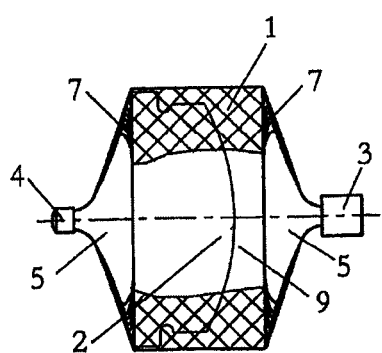
FIG. 40 is a integral structure diagram of the fourth embodiment of the present invention.
Figure 41:
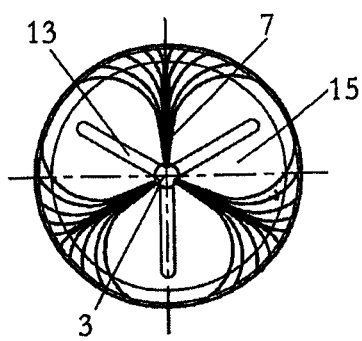
FIG. 41 is a right view of the invention in FIG. 40.

By referring to FIGS. 40-41, diaphragm 2 is placed in the cylindrical stent 1 with a front clip 4 and a rear clip 3 arranged symmetrically (see FIG. 40). This stent has three openings 5. The head of diaphragm 2 presents a spherical surface, and the gap on the diaphragm 2 is a triangular gap 13. This triangular gap is staggered with the three openings 5 (see FIG. 41), and the cylindrical stent 1 can be released or recovered in a double direction through the front clip 4 or the rear clip 3.

Figure 42:
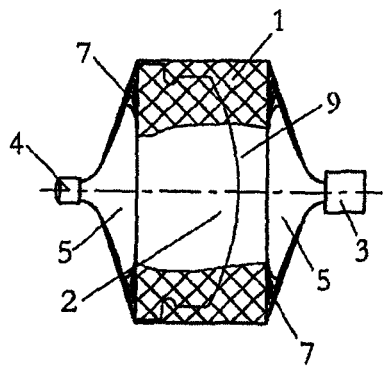
FIG. 42 is the integral structure diagram of the Embodiment 5 of the present invention.
Figure 43:
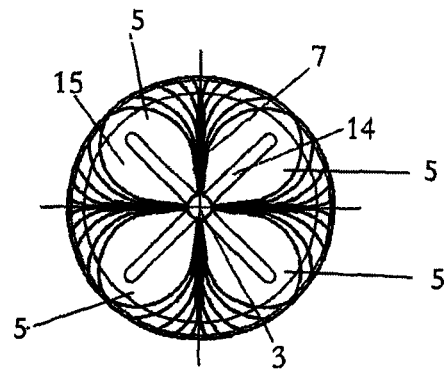
FIG. 43 is a right view of the invention in FIG. 42.

Referring to FIGS. 42-43, diaphragm 2 is placed in the cylindrical stent 1 with a front clip 5 and a rear clip 4 arranged symmetrically (see FIG. 42). This stent has four openings 5. The head of diaphragm 2 presents a spherical surface, and the gap on the diaphragm 2 is a cross-shaped gap 12. This cross-shaped gap is staggered with the four openings 5 (see FIG. 43), and the cylindrical stent 1 can be released or recovered in a double direction through the front clip 4 or the rear clip 3.

Figure 44:
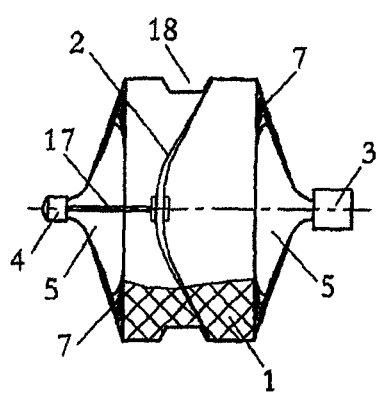
FIG. 44 is an integral structure diagram of the sixth embodiment of the present invention.
Figure 45:
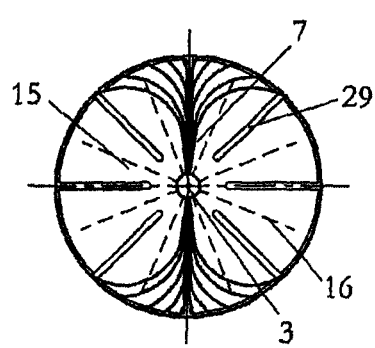
FIG. 45 is a right view of the invention in FIG. 44.
Figure 46:
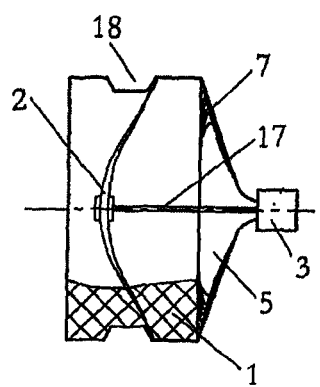
FIG. 46 is an integral structure diagram of the seventh embodiment of the present invention.
Figure 47:
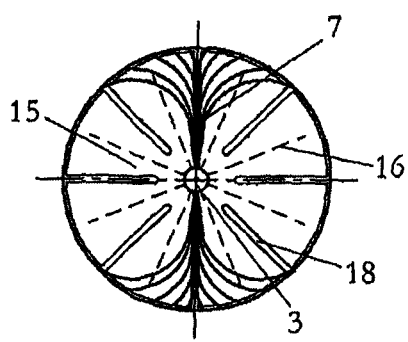
FIG. 47 is a right view of the invention in FIG. 46.
Figure 48:
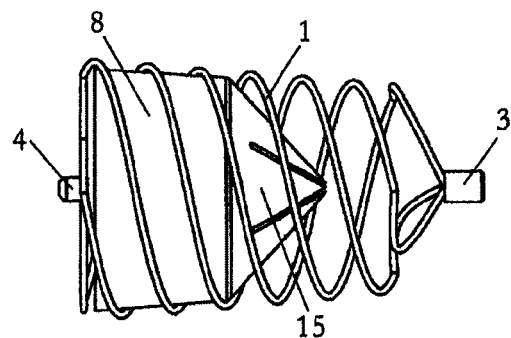
FIG. 48 is an integral structure diagram of the eighth embodiment of the present invention.
Figure 49:
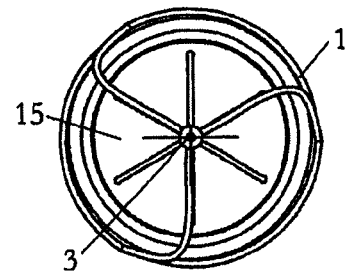
FIG. 49 is a right view of the invention in FIG. 48.
Figure 50:
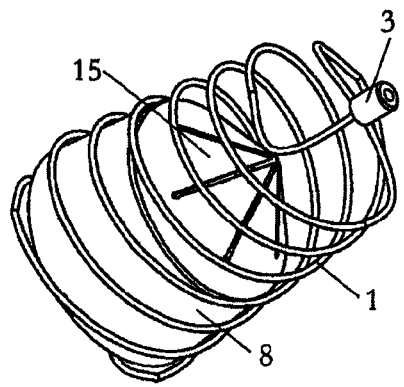
FIG. 50 is a solid state diagram of the invention in FIG. 48.
Figure 51:
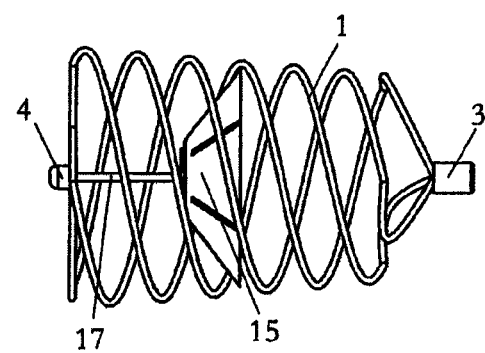
FIG. 51 is an integral structure diagram of a ninth embodiment of the present invention.
Figure 52:
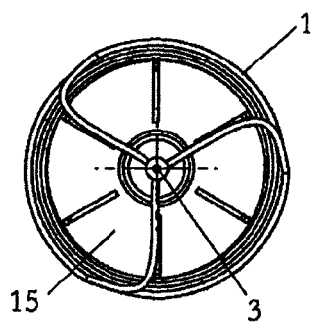
FIG. 52 is a right view of the invention in FIG. 51.

Referring to FIGS. 44-45, one end of the cylindrical stent 1 forms two openings 5 after two alloy wire bundles 7 are fixed by the front clip 4, while the other end forms two openings 5 after two alloy wire bundles are fixed by the rear clip 3. The umbrella diaphragm 2 is placed in the cylindrical stent 1. One end of the metal rod 17 is connected with the front clip 4, while the other end is connected with the central part of the umbrella top of the diaphragm 2. The peripheral edge of the umbrella body tightly holds out against the embolic wall surface (see FIG. 44) formed by the sunken ring 18 of the cylindrical stent 1. The embolic wall surface forms a seal to the diaphragm 2 (similar to a valve cutting edge), while the metal rod 17 stretches the diaphragm 2, to make it kept at an umbrella state. When the gas flow or liquid enters from the front clip 4, the gas or liquid gathers around the periphery of the umbrella top of the diaphragm 2, so the spring piece 15 formed by the gaps 29 bends toward the direction of the rear clip 3 under compression, and the outer edge of the spring piece is disengaged with the inner wall surface of the sunken ring 18, so the umbrella diameter of the umbrella diaphragm 2 shrinks and then forms an annular opening. The gas flow or liquid flows out from this annular opening. In case of backflow, the gas flow or liquid tightly compresses the edge of the spring piece 15 together with the embolic wall surface of the sunken ring 18, so as to form a sealing face and then obstruct the flow of the gas or liquid. The metal rod 17 stretches and supports the diaphragm 2 when the gas or liquid flows forward or backward; the said metal rod 17 can extend outward from the internal part of the umbrella body and then is firmly connected with the rear clip 3 of the cylindrical stent 1, looking like an opened umbrella. The metal rod 17 stretches and supports the diaphragm 2 when the gas or liquid flows forward or backward (see FIG. 46), to make it kept at an umbrella state.

By referring to FIGS. 48-53, the diaphragm 2 is placed in the spiral cylindrical stent 1. The shape of the diaphragm 2 can be any of the said diaphragms 2, while the cylindrical section 8 of the diaphragm 2 is also in a frustum shape, so as to be matched with the spiral cylindrical stent. If the diaphragm 2 is in an umbrella shape, the umbrella diameter of the diaphragm 2 needs to accord with the diameter of some spiral coil of the spiral cylindrical stent, which can be determined by the length of the metal rod 17.

The said diaphragms 2 are applicable to the said threadlike cylindrical stent, the net-like cylindrical stent etched by laser and the spiral cylindrical stent, and can be selectively matched according to the required gas or liquid flow rate. The metal wire support 16 which can enhance the elastic deformation and strength of the spring piece can be arranged inside or on the surface of the spring piece 15.

What is claimed is:

1. A recoverable valve stent, comprising:
a cylindrical stent made up of memorial alloy material in which an elastic diaphragm is arranged, wherein there is at least one gap on the diaphragm so that the diaphragm forms a flexible spring piece, one end of the cylindrical stent is provided with a fixed rear clip which is used for fixing the cylindrical stent being structured with the memorial alloy material and is equipped with screwthreads which can be connected to a conveyor,
wherein a thread of the memorial alloy material is weaved into the cylindrical stent and forms at least two bundles of alloy wire which are fixed with the rear clip locating at the axis of the cylindrical stent, so that the end of the cylindrical stent fixed with the rear clip forms at least two openings in sub-oval shape.

2. A recoverable valve stent, comprising:
a cylindrical stent made up of memorial alloy material in which an elastic diaphragm is arranged, wherein there is at least one gap on the diaphragm so that the diaphragm forms a flexible spring piece, one end of the cylindrical stent is provided with a fixed rear clip which is used for fixing the cylindrical stent being structured with the memorial alloy material and is equipped with screwthreads which can be connected to a conveyor,
wherein a thread of the memorial alloy material is weaved into the cylindrical stent and forms at least three or four bundles of alloy wire which are fixed with the rear clip locating at the axis of the cylindrical stent, so that the end of the cylindrical stent fixed with the rear clip forms at least three or four openings.

3. The recoverable valve stent according to claim 1, wherein the other end of the cylindrical stent is provided with a front clip, and the front clip and the rear clip are arranged symmetrically or asymmetrically.

4. The recoverable valve stent according to claim 2, wherein the other end of the cylindrical stent is provided with a front clip, and the front clip and the rear clip are arranged symmetrically or asymmetrically.

5. A recoverable valve stent, comprising:
a cylindrical stent made up of memorial alloy material in which an elastic diaphragm is arranged, wherein there is at least one gap on the diaphragm so that the diaphragm forms a flexible spring piece, one end of the cylindrical stent is provided with a fixed rear clip which is used for fixing the cylindrical stent being structured with the memorial alloy material and is equipped with screwthreads which can be connected to a conveyor; and
wherein the diaphragm is provided with a cylindrical section which is fit to the cylindrical stent, and one end of the cylindrical section is arranged integrally with a convex surface raising towards the center of a circle which has one unclosed round gap, so that the flexible spring piece is formed.

6. A recoverable valve stent, comprising:
a cylindrical stent made up of memorial alloy material in which an elastic diaphragm is arranged, wherein there is at least one gap on the diaphragm so that the diaphragm forms a flexible spring piece, one end of the cylindrical stent is provided with a fixed rear clip which is used for fixing the cylindrical stent being structured with the memorial alloy material and is equipped with screwthreads which can be connected to a conveyor,
wherein the diaphragm is provided with a cylindrical section which is fit to the cylindrical stent, and one end of the cylindrical section is arranged integrally with a convex surface raising towards the center of a circle which has two arch gaps symmetrically arranged and connected by a straight gap so as to form an I-shape gap, so that the spring piece is separated into two bendable sections.

7. A recoverable valve stent, comprising:
a cylindrical stent made up of memorial alloy material in which an elastic diaphragm is arranged, wherein there is at least one gap on the diaphragm so that the diaphragm forms a flexible sprinq piece, one end of the cylindrical stent is provided with a fixed rear clip which is used for fixing the cylindrical stent being structured with the memorial alloy material and is equipped with screwthreads which can be connected to a conveyor,
wherein the diaphragm is provided with a cylindrical section which is fit to the cylindrical stent, and one end of the cylindrical section is arranged integrally with a convex surface raising towards the center of a circle which has three branched gaps being arranged equiangularly and extending from the center of a circle towards a periphery of the diaphragm, so that the spring piece is separated into three bendable sections.

8. A recoverable valve stent, comprising:
a cylindrical stent made up of memorial alloy material in which an elastic diaphragm is arranged, wherein there is at least one gap on the diaphragm so that the diaphragm forms a flexible spring piece, one end of the cylindrical stent is provided with a fixed rear clip which is used for fixing the cylindrical stent being structured with the memorial alloy material and is equipped with screwthreads which can be connected to a conveyor, wherein the diaphragm is provided with a cylindrical section which is fit to the cylindrical stent, and one end of the cylindrical section is arranged integrally with a convex surface raising towards the center of a circle which has a cross-branched gaps extending from the center of the circle towards periphery of the diaphragm, so that the spring piece is separated into four bendable sections.

9. The recoverable valve stent according to claim 6, wherein each section of the spring piece of the diaphragm is provided with a curved sunken part.

10. The recoverable valve stent according to claim 9, wherein the thickness of the spring piece gradually diminishes from circumference to a convex center of the circle, and there is a cylinder at the intersecting position of the cylindrical section and the convex surface.

11. The recoverable valve stent according to claim 10, wherein there are metal wire supports which can increase elastic deformation and strength of the spring piece, and are arranged inside of the spring piece or on its surface.

12. A recoverable valve stent, comprising:
a cylindrical stent made up of memorial alloy material in which an elastic diaphragm is arranged, wherein there is at least one gap on the diaphragm so that the diaphragm forms a flexible spring piece, one end of the cylindrical stent is provided with a fixed rear clip which is used for fixing the cylindrical stent being structured with the memorial alloy material and is equipped with screwthreads which can be connected to a conveyor;
wherein the other end of the cylindrical stent is provided with a front clip, and the front clip and the rear clip are arranged symmetrically or asymmetrically,
wherein the spring piece has a raised center of a circle which has a diameter matching that of the cylindrical stent, the spring piece is connected with one of the front clip or the rear clip of the cylindrical stent by a metal rod, and at least two gaps which extend from the position near the center of the circle to an edge of the spring piece are arranged so as to separate the spring piece into at least two sections.

* * * * *